United States Patent [19]

Pizzarello

[11] 4,055,992
[45] Nov. 1, 1977

[54] BEAM LEAD TESTING APPARATUS

[75] Inventor: Frank A. Pizzarello, Santa Ana, Calif.

[73] Assignee: Rockwell International Corporation, El Segundo, Calif.

[21] Appl. No.: 696,676

[22] Filed: June 16, 1976

[51] Int. Cl.² .......................................... G01N 19/04
[52] U.S. Cl. ................................................. 73/88 B
[58] Field of Search .................. 73/88 B, 101, 150 R, 73/150 A, 103, 88 B

[56] References Cited

U.S. PATENT DOCUMENTS

| | | | |
|---|---|---|---|
| 3,091,960 | 6/1963 | Houda, Jr. | 73/95 |
| 3,127,766 | 4/1964 | Wolle | 73/88 B |
| 3,376,736 | 4/1968 | Emery, Jr. | 73/88 B X |
| 3,564,911 | 2/1971 | Slemmons et al. | 73/150 A X |
| 3,580,065 | 5/1971 | Strittmater et al. | 73/95 |
| 3,611,795 | 10/1971 | Goldmann et al. | 73/88 B |

Primary Examiner—Charles A. Ruehl
Attorney, Agent, or Firm—L. Lee Humphries; H. Fredrick Hamann; G. Donald Weber, Jr.

[57] ABSTRACT

An apparatus for testing the bond strength of beam leads is disclosed. The present invention involves testing apparatus that includes a movable table having a probe, a mounting bar adjacent said movable table having a base with an angled surface for mounting microcircuit devices having beam leads and a driving assembly that attaches to said mounting bar for rotating said mounting bar. The device chips are mounted on the mounting bar. The table is positioned towards and under the beam leads extending from the device, the probe on the index table is precisely adjusted to clamp the desired beam lead against the table. The driving assembly is activated to move the mounting bar away from the table until the beam lead is stripped therefrom. A force gage which is attached to the driving assembly measures the force required to strip the beam lead away from the device chip.

8 Claims, 2 Drawing Figures

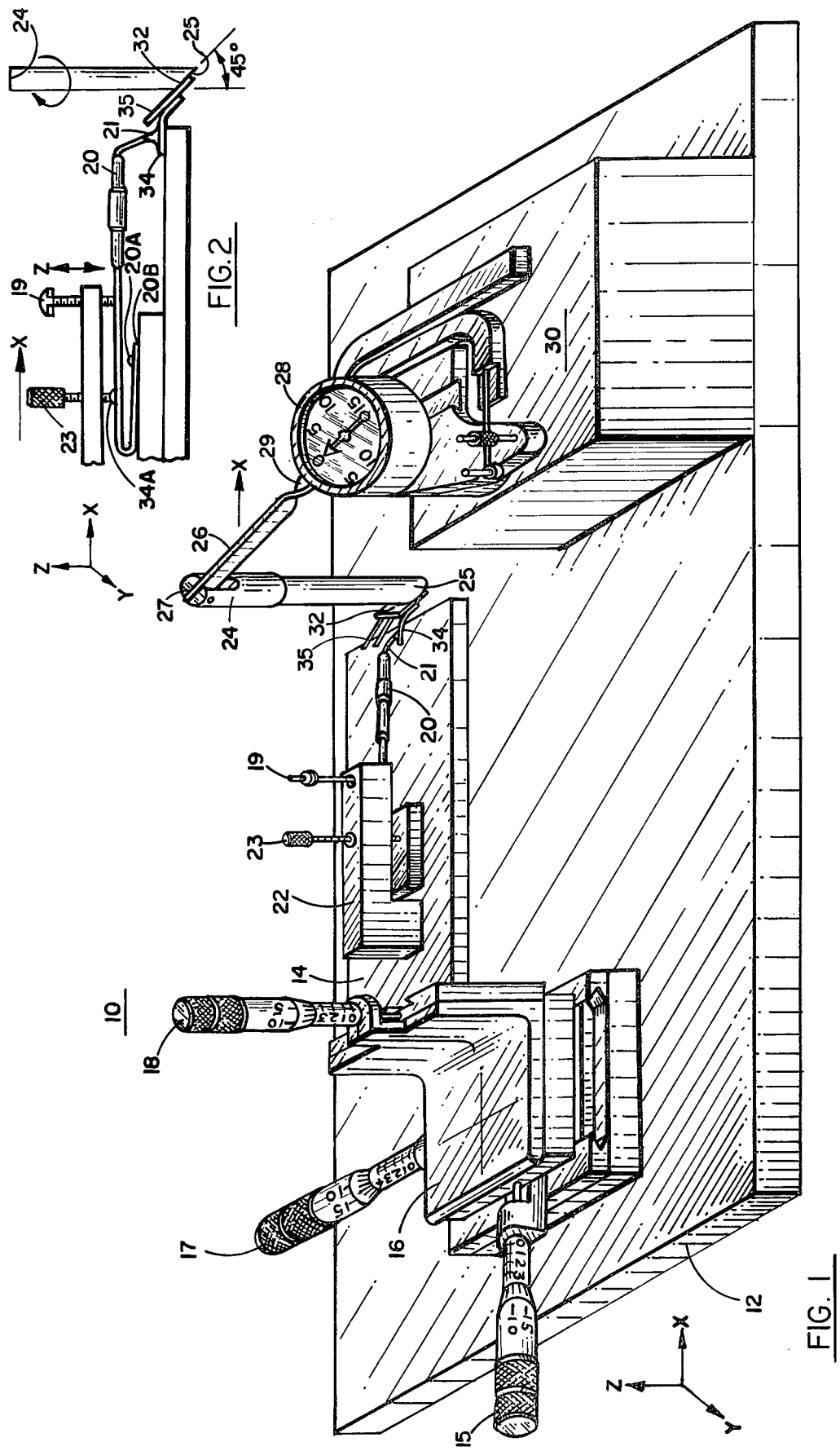

BEAM LEAD TESTING APPARATUS

BACKGROUND OF THE INVENTION

1. Field of the Invention

This invention relates to apparatus for testing MOS-LSI devices and, more particularly, to measuring the strength of bonds which join the beam leads and the device chips.

2. Description of the Art

There exists a need for test equipment that can accurately test and measure the bond strength and observe the mode of failure of individual beam leads. To ascertain the reliability of the fabricated beam leads at least two factors must be measured, the beam strength and the rate of aging. The bond pull strength is critical in determining both of these factors hence a test apparatus that can measure both the force necessary to break a bond and observe the mode of failure is desirable. Integrated circuit chips are generally very small, fragile and involve a plurality of beam leads that are bonded to the chips. Presently, bond test equipment lacks the capability of gripping each individual minute beam lead and stressing it under varied geometrical conditions until failure occurs. That is, since the beam leads are small and intricate to handle, it is difficult to position the test equipment in relation to the chips and the beam leads to hold one end and pull the beam lead until it fails and simultaneously measure the force required for such failure. Adams et al, in *Review of Scientific Instruments*, November, 1968, p. 1768, teaches how to grip fine wires by using a small drop of apiezon wax on the end of a thin probe, then manipulating the probe mechanically to make contact with the wire to be tested. A heating element is brought into contact with the probe and current is turned on causing the wax to melt, capillary attraction causes the wax to surround and "grab" the wire, thus producing a rigid and strong bond. While this means appears to be suitable for gripping fine wires, it subjects the wire to heat from a heating element with electric current and also requires the use of wax. Both of these factors are time consuming and could distort the true force required to test a fine wire.

Another known apparatus for testing the bond strength between two laminated layers of material is taught by A. R. Mancini in U.S. Pat. No. 3,019,644. Mancini discloses the use of an electric motor and a force gage to measure the stripping force of two laminated layers. The apparatus consists of a rigid frame having a common drive shaft connected to several structural elements including sprocket gears, sprocket chain, drive pulleys, idler pulleys, a bifurcated support member, hook and a spring scale. Both layers are slowly advanced by the mechanization in opposite directions until there is a failure, the spring scale measures the force. This type of apparatus is too cumbersome and complex to measure the bond strength of minute beam leads. Also, gripping the beam leads is difficult with a hook.

U.S. Pat. No. 2,377,869 by M. A. Elliott also teaches the use of an electric motor and drive members to test the deep drying properties of insulating materials. This apparatus includes various electrical components that make up a measuring part of the apparatus. The specimen to be tested is held between two clamps. One clamp is suspended from a tension bar. The first clamp is drawn away from the second clamp by a drive motor. The meausring part of the apparatus measures the voltage change with respect to the deflection of the tension bar which is proportional to the actual tension to which the specimen is subjected. This apparatus is also quite complex, and it is doubtful that it could be adapted to test beam leads.

McGrath, U.S. Pat. No. 3,702,437 discloses a micrometer driver positioning assembly for moving and supporting an electronic assembly during diagnosing and repairing of devices of said electronic assembly. This apparatus lacks a means for clamping the small wires and the micrometer driving assembly does not slide around independently of the micrometer which is used for fine positioning. ;p Still another apparatus, the "Hunter Terminal Pull Tester" described in Bulletin 750e of Hunter Spring Company, dated September, 1961, tests electrical connectors. This apparatus utilizes an air motor having a moving piston which connects directly to a set of serrated clamping jaws for gripping the wire. An indexing disc provides holding notches for terminals of varying sizes which is mounted to a force gage. Once the crimped terminal or connector is secured in the notch on the tension head of the force gate, and the wire is placed between the open jaws of the air motor, the jaws close around the wire and the piston moves at the preset speed. The piston pulls the jaws and wire until the crimped connection fails or the insulation breaks. The force gage indicates the force exerted to cause the instant failure. While the Hunter tester appears to be adequate for production type terminals, more precise equipment and means is required for securing the minute integrated chips, clamping of the fine beam leads, measuring the beam lead strength and determining the mode of failure.

SUMMARY OF THE INVENTION

This invention relates to an apparatus for testing the bond strength of beam leads. The instant invention utilizes a moving table having X, Y and Z movement. An adjustable probe is attached to the table and has independent vertical and horizontal movement for precisely clamping a beam lead against the table. A mounting bar having a base with an angle of 0° to 90° to the horizontal is used for securing the beam lead chip to the angled surface. The table is moved towards the chip until the table edge is under the beam leads. The probe is then manipulated to clamp a selected beam lead. The mounting bar is connected to a test bar which is attached to a driving assembly having a force gage. The driving assembly moves the test bar in a circular direction away from the index table until the beam lead breaks the bond from the chip. The force gage measures the force that caused this failure. A microscope may also be utilized to observe the mode of failure.

BRIEF DESCRIPTION OF THE DRAWINGS

FIG. 1 illustrates the configuration of a preferred embodiment of a beam lead tester which represents this invention including the arrangement of clamp means and a mounting bar securing a chip.

FIG. 2 is a side view of a beam lead clamped on the index table in abutment with the supported chip in accordance with the instant invention illustrated in FIG. 1.

DETAILED DESCRIPTION

Referring to FIG. 1, there is illustrated the various components embodying principles of the present invention, which include moving table 14 and a mounting bar 24. Testing apparatus 10 is secured on a suitable table 12 to assure that during testing of beam leads there is substantially no vibration or wobbling of the various components that make up the testing apparatus. In accordance with one embodiment, moving table 14 has a generally rectangular configuration with a flat surface having an indexing mechanism 16 attached at one end thereof as shown in FIG. 1. Indexing mechanism 16 includes micrometers 15, 17 and 18 which control the rough movement of table 14 relative to table 12 in the X, Y and Z direction, respectively. The indexing mechanism 16 permits table 14 to be positioned towards mounting bar 24. Table 14 also includes a probe assembly 22 for clamping the individual beam leads against the top of table 14.

Probe assembly 22 includes probe 20 and tip 21 which is attached to probe 20. In a preferred embodiment, probe 20 extends substantially horizontal over the surface of table 14 to be able to position tip 21 over a beam lead and clamp it against the surface of table 14. Probe 20 has independent X, Y and Z movement by virtue of adjusting screws 19 and 23 and will be described subsequently. These adjustments permit precise positioning of tip 21. In one embodiment, tip 21 is curved and flares out to a flat tip (See FIG. 2). That is, the bottom surface of tip 21 is flat, which readily permits clamping of a beam lead against the surface of table 14 without damaging the beam leads. The probe assembly 22 may be secured to table 14 by mechanical, magnetic or other suitable means.

Adjacent table 14 is mounting bar 24, having a bottom surface 25 cut at an angle. Mounting bar 24 may be formed of any suitable material such as metal. The angled surface can be cut at any desired angle from 0° to 90° to meet the desired test specifications. The embodiment shown utilizes a 45° angled surface for the purpose of demonstrating the average peeling force normally imposed on the bonded chips. It is to be understood that other angled surfaces or even a flat surface may be utilized for the mounting surface. Device 32 is shown glued to the angled surface 25 with the beam leads 35. The top portion of mounting bar 24 includes a rotating arm 26 which is connected to force gage 28. In one embodiment, rotating arm 26 is formed of a metal bar having a 90° twist. The 90° twist is for convenience in that the portion that attaches to the top of mounting bar fits vertically in the slot 27 in this arrangement. Of course, other mounting arrangements can be utilized as well. The other end 29 engages into a horizontal slot arrangement in force gage 28. Force gage 28 is connected to a vertical shaft, not shown, which shaft is driven by a motor housed in box 30. Box 30 is also secured to table 12 by any suitable means as suggested in FIG. 1.

Referring to FIG. 2, there is better illustrated device chip 32 mounted with an adhesive to the angled surface 25 of mounting bar 24. The beam lead 34 to be tested extends from chip 32 at 45° to the horizontal table 14 as does lead 35. The beam leads that are to be tested may be fabricated from copper, aluminum or beryllium copper foil similar to the method taught in copending application entitled "Method of Fabrication A Beam Lead Flexible Circuit" by Joseph Shaheen et al, filed Dec. 9, 1975, and assigned to the common assignee.

FIG. 2 better illustrates the configuration of probe 20 as it extends rearward from tip 21 beyond adjusting screw 23 in a serpentine fashion, reverting towards tip 21, its end 20A resting on a pivot point 20B. By virtue of pivot point 20B, screw 19 can adjust probe 20 in the Z direction. Screw 23 has a ball bearing tip 23A which seats on the rearward portion of probe 20. This arrangement results in a circular motion of probe 20 when screw 23 is adjusted, thus providing probe 20 with movement in the X and Y direction. It should be noted that the adjustments of probe 20 are rather minute and precise since table 16 positions probe 20 substantially over the area of the desired beam lead. Thus, it can be seen how readily tip 21 may be manipulated to clamp a beam lead.

Also illustrate in FIG. 2 is how probe tip 21 flares out and has a flat bottom surface. The flattened surface, of course, assures that the desired beam lead will be clamped against the surface of table 14. FIG. 2 also shows how tip 21 extends horizontally out afrom probe 20 then sharply downward. Tip 21 may be readily replaced in case the tip is worn out or damaged. In one embodiment during the aligning of table 14 and manipulating of probe 20, a microscope (not shown) can be utilized to magnify the clamping of the beam lead. That is, the microscope can be positioned over the probe area to assure that the beam lead is properly clamped by the flat tip 21.

Once the desired beam lead 34 is clamped as shown in either FIG. 1 or 2, motor 30 is energized, the vertical shaft turns, tightening the coil spring (not shown) of the force gage 28 which in turn moves rotating arm 26 a horizontal circular path (X-Y) plane when the breaking strength of the beam lead is exceeded. When rotating arm 26 moves, it also moves mounting bar 24 in clockwise path (as indicated by the arrow in FIG. 2) away from table 14 in a slight circular motion, X-direction for the purpose of peeling away the beam lead. Force gage 28 measures the force required to strip the beam lead 34 from chip 32. To assure that no kinetic forces are applied to the beam lead being tested, the rate of tightening the coil spring of force gage 28 is slowly and incrementally applied. In one application of the instant invention, the spring is tightened at a rate of 0.66 revolutions per minute. It has been found by experimentation that such rates of tightening substantially prevent "jerking and snapping" of the beam lead. These rates of tightening can be attained by utilizing a variable slow speed motor.

In another embodiment for determining the bond strength of beam leads, gage 28 may be a strain gage which produces some change in its electrical characteristics as a function of the applied force. That is, the electrical output from this system can be calibrated to yield a graphical representation of the applied force or stress versus time or displacement during the test mode until failure occurs. An apparatus which incorporates this means of determining the mode of failure can also reveal whether creep occurs before failure and still measure the magnitude of the effect. Therefore, a stress or strain behavior, whether linear or non-linear, up to the time of failure can be determined with this invention.

The failure mode can be microscopically observed while the force is applied by utilizing the microscope previously discussed. The failure of individual bonds can vary but generally fall within the limits of peeling from the bonding pads to tensile elongation and failure. For example, gold beam leads on repeated tests show failure exclusively by peeling from the bond pad, whereas aluminum beam leads show tensile extension before breaking at the weakest region.

In one actual operation, a device chip 32 having beam leads 3.0 mils. wide and 6.0 mils. long was mounted on angled surface 25 of mounting bar 24 with an adhesive. Once chip 32 is mounted, table 14 is moved towards and under the beam leads extending from chip 32 by manipulating micrometers 15, 17 and 18 in the X, Y and Z directions. For the clamping of the beam lead, probe 20 is precisely and independently of table 14 manipulated in the Z direction by adjusting screw 19 and in the X or Y direction by adjusting screw 23 until the desired beam lead 34 is clamped by flat tip 21 against the surface of table 14 as shown in either FIG. 1 or FIG. 2. The motor 30 is now energized, the vertical shaft tightens the coil spring of force gage 28, which in turn applies a tensile force on arm 26 in a direction away from the table in the X direction until the breaking strength of the beam lead is exceeded. As the force is applied, the force gage coil spring is tightened which causes the force gage to register the required force necessary to break a beam lead. This mode of failure can be micorscopically observed. After the beam lead fails, actual movement of the rotating arm and mounting bar is but a few degrees.

Thus, there is shown and described a preferred apparatus and method for measuring the bond strength of individual minute beam leads and determining the respective mode of failure for each beam lead. The instant invention simplifies the handling of the fragile beam leads and assures accuracy in determining the beam lead strength and the mode of failure.

It will be appreciated by those skilled in the art that the invention may be carried out in various ways and may take various forms and embodiments other than the illustrated embodiments heretofore described.

Having thus described a preferred embodiment of this invention, what is claimed is:

1. An apparatus for testing the strength of beam leads bonded to a device comprising:
    table means;
    clamp means for holding beam leads to said table means;
    a mounting bar adjacent said table means and having means for mounting said device;
    said table means and said mounting bar being movable relative to each other;
    means for rotating said mounting bar such that the beam leads held to said table means are broken from said device; and
    means for measuring the force applied by said means for rotating to cause said beam leads to be broken from said device.

2. The apparatus recited in claim 1 including adjusting means for moving said table means in the X, Y and Z directions.

3. The apparatus recited in claim 1 wherein said clamp means includes a probe having a tip with a flat surface; and
    independent adjusting means for manipulating said probe in the X, Y and Z direction.

4. The apparatus recited in claim 1 wherein the base of said mounting bar has an inclination of from 0° to 90° to the horizontal for mounting said device.

5. An apparatus as recited in claim 1 wherein said means for measuring includes a force gage.

6. An apparatus as recited in claim 5 wherein said means for measuring includes a strain age for sensing some change in its electrical characteristics as a function of the applied force from said means for rotating thereby yielding an output signal that can be converted to a graphical representation indicating either the applied force, stress versus time, or displacement during the movement of said mounting bar.

7. An apparatus as recited in claim 1 wherein said means for rotating includes driving means connected to said measuring means; said driving means applying force on said measuring means within a range from 0.01 to 01.0 revolutions per minute, thereby causing said mounting bar to rotate in a horizontal circular path away from said movable table.

8. An apparatus for testing the strength of beam leads bonded to a device comprising:
    a rigid member for supporting the components of said apparatus;
    a table having an index mechanism mounted on said rigid member for controlling the movement of said table in the X, Y or Z direction;
    a probe assembly mounted on said table having a probe with a flat tip for clamping said beam leads and having independent X, Y and Z movement;
    a mounting bar vertically mounted adjacent said table and having an inclination on its bottom portion to the horizontal for mounting said device;
    a rotating member horizontally connected to the top portion of said mounting bar;
    measuring means connected to said rotating member; and
    driving means for applying force to said measuring means for causing said rotating member and said mounting bar to slowly rotate away from said table in a uniform manner, said measuring means registering the required force to move said mounting bar and the stripping of said beam lead from said device.

* * * * *